United States Patent
Edwards et al.

[11] Patent Number: 6,001,094
[45] Date of Patent: Dec. 14, 1999

[54] IMPLANTABLE SOLUBLE ELECTRODE SYSTEM

[75] Inventors: Stuart D. Edwards, Portola Valley, Calif.; Ronald Lax, Palm City, Fla.

[73] Assignee: Vidacare International, Inc., Portola Valley, Calif.

[21] Appl. No.: 09/004,605

[22] Filed: Jan. 8, 1998

Related U.S. Application Data

[60] Provisional application No. 60/034,195, Jan. 9, 1997.

[51] Int. Cl.⁶ .................................................. A61B 17/39
[52] U.S. Cl. ................... 606/41; 606/49; 607/99; 607/105; 607/113
[58] Field of Search .............. 606/41, 49; 607/99, 607/105, 113, 116; 600/377

[56] References Cited

U.S. PATENT DOCUMENTS

| | | | |
|---|---|---|---|
| 4,141,365 | 2/1979 | Fischell et al. | 600/377 |
| 4,291,707 | 9/1981 | Heilman et al. | 128/784 |
| 4,827,940 | 5/1989 | Mayer et al. | 600/377 |
| 4,936,301 | 6/1990 | Rexroth et al. | 606/49 |
| 5,236,413 | 8/1993 | Feiring | 607/116 |
| 5,797,903 | 8/1998 | Swanson et al. | 607/99 |

FOREIGN PATENT DOCUMENTS

| | | | |
|---|---|---|---|
| 0 204 640 A1 | 12/1986 | European Pat. Off. | A61N 1/40 |
| 0 316 995 A1 | 5/1989 | European Pat. Off. | A61N 1/05 |
| WO85/02779 | 7/1985 | WIPO | A61N 5/00 |
| WO94/17856 | 8/1994 | WIPO | A61N 5/02 |

*Primary Examiner*—Lee Cohen
*Attorney, Agent, or Firm*—David J. Weitz; Wilson Sonsini Goodrich & Rosati

[57] ABSTRACT

An implantable electrode is provided for treating tissue in a patient with energy. In one variation of this embodiment, the implantable electrode includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a soluble and porous material which at least partially surrounds the electrode core and becomes conductive when contacted with an energy conducting liquid. According to this variation, the shaft also includes a lumen for delivering energy conducting liquid from outside the body to the head.

17 Claims, 5 Drawing Sheets

IMPLANTABLE SOLUBLE ELECTRODE SYSTEM

CROSS-REFERENCE TO RELATED APPLICATION

This application claims priority to the U.S. provisional application entitled IMPLANTABLE ELECTRODE, Ser. No. 60/034,195, filed Jan. 9, 1997, and invented by Stuart D. Edwards and Ronald Lax.

BACKGROUND OF THE INVENTION

1. Field of the Invention

This invention relates to an electrode for damaging tissue within a patient's body and more particularly to an electrode which damages tissue by delivering a conductive fluid and radio frequency energy to a selected site within a patient's body.

2. Description of Related Art

It is often desirable to damage tissue at selected sites within the body without open surgery. For instance, when treating malignant tumors, abscesses, or infected tissue, a physician wants to destroy the tissue within a patient's body. In open surgery the physician opens the patient and attempts to physically remove the targeted tissues. However, open surgery can cause additional complications such as infection. Thus, several closed surgery techniques have been developed for damaging tissue. For instance, radiating the patient from an external source has been tried. Unfortunately, since the source is external, the radiation can not be sufficiently localized to the targeted tissue, thus, healthy tissue which has not been targeted can be damaged.

A recent technique which provides more localized treatment of the target tissue involves introducing a radio frequency (RF) electrode into the target tissue. In this technique, the physician places the electrode within the target tissue using techniques such as fluoroscopy, ultrasound, or manual palpitation. The physician then applies RF energy to the electrode which heats the tissue surrounding the electrode. Tissue is generally sensitive to heat such that high levels of heat or simply sustained heat can damage or destroy it. Once the physician has applied a desired amount of energy, the treatment is complete and the physician withdraws the electrode.

There are several difficulties with this technique. For instance, tissue adjacent to the electrode begins to desiccate very quickly, particularly when there is a high current density on the surface of the electrode. Once the tissue desiccates, the ability of that tissue to conduct RF energy is reduced. Thus, once the tissue becomes desiccated around the electrode, the ability of the electrode to treat tissue remote from the surface of the electrode is diminished. As a result, this technique is most effective for treating tissues which are closest to the surface of the electrode.

Another difficulty can arise when the physician must perform successive treatments. Often, the first treatment does not completely destroy the target tissue and additional treatments are required. To perform additional treatments, the physician must attempt to reinsert the electrode into the same target tissue. To do this, the physician often wants to puncture the same point on the patient's skin. However, scar tissue is often present from the previous surgery, thus, the physician usually does not want to puncture the same point again and must puncture the skin in a new location. This means the electrode will not approach the target site from the same angle and may result in imprecise placement of the electrode.

For the above reasons, there is a need for a method and device which can locally damage target tissue without open surgery. The method and device should allow the physician to easily treat tissue remote from the surface of the electrode. Further, the method and device should allow a physician to easily treat the same area of the target site each time a treatment is performed.

SUMMARY OF THE INVENTION

It is an object of the present invention to provide a method and apparatus for locally damaging target tissue.

It is an object of the present invention to provide a method and apparatus for locally damaging target tissue without performing open surgery.

It is an object of the present invention to provide a method and apparatus which damages tissue by using an electrode.

It is an object of the present invention to provide a method and apparatus which damages tissue by using an electrode which damages tissue remote from the surface of the electrode.

It is an object of the present invention to provide a method and apparatus which damages tissue by using an electrode which can be left in the patient for use in subsequent treatments.

These objectives and others are provided by the methods and devices provided herein for locally damaging tissue.

An implantable electrode is provided for treating a tissue site in a patient with energy. In one embodiment, the implantable electrode includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a porous material which at least partially surrounds the electrode core and becomes conductive when contacted with an energy conducting liquid. The shaft also includes a lumen for delivering energy conducting liquid from outside the body to the head. In one variation, the head is formed at least in part by a material which is both porous and soluable.

A trocar is also provided for delivering to a tissue site an implantable electrode having a shaft which extends from the tissue site to outside a body of a patient. In one embodiment, the trocar includes a hollow member having a sharpened distal end capable of being introduced into a patient and a longitudinal channel extending to a distal end of the hollow member within which an implantable electrode may be positioned, and a slot extending along a length of the longitudinal channel through which a shaft of the implantable electrode can pass and the trocar can be removed without removing the implantable electrode.

A kit and an assembly are also provided for delivering an implantable electrode to a tissue site which includes the combination of an implantable electrode and trocar according to the present invention.

A method is also provided for introducing an implantable electrode at a selected tissue site. According to one variation of the method, an implantable electrode is provided which includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a porous material which at least partially surrounds the electrode core and becomes conductive when contacted with an energy conducting liquid wherein the shaft includes a lumen for delivering energy conducting liquid from outside the body to the head. The implantable electrode is placed in a trocar which has a sharpened distal end capable of being introduced into a patient, a hollow member having a longitudinal channel within which an implantable electrode may be positioned, and a slot extending from the distal end of the trocar along a length of the longitudinal channel through which the shaft of the implantable electrode can pass. The trocar is inserted into a patient such that the head of the implantable electrode is positioned at the selected tissue site. The trocar is then removed while passing the removable electrode shaft through the longitudinal channel such that the head of the implantable electrode remains positioned at the selected tissue site and a proximal end of the shaft extends outside the body.

A method for damaging tissue at a selected tissue site is also provided. According to one embodiment of the method, an implantable electrode is provided at a selected tissue site which includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a porous material which at least partially surrounds the electrode core and becomes conductive when contacted with an energy conducting liquid. The shaft includes a lumen for delivering energy conducting liquid from outside the body to the head. Energy conducting liquid is delivered through the lumen to create a region containing a conductive solution in the vicinity of the head. In one embodiment, the head is also formed of a soluble material which is at least partially dissolved by the energy conducting liquid. Energy from an external energy source is then delivered to the selected tissue site via the energy conducting liquid.

In another embodiment, a method is provided for damaging tissue at a selected tissue site at different times using a single implantable electrode. According to one variation of this method, tissue is damaged at a selected tissue site using an implantable electrode according to a method of the present invention. A period of time comprising minutes, hours, days, weeks months or years is then allowed to pass. The tissue at the selected tissue site is then damaged again using the same implantable electrode according to a method of the present invention.

DETAILED DESCRIPTION

The invention relates to a method and apparatus for treating tissue in a patient with energy in order to damage the tissue using an electrode which can be left within the patient and used repeatedly over time.

In one embodiment, an electrode is provided for treating tissue in a patient with energy. The electrode includes a shaft having a length sufficient to extend from outside the body of the patient to adjacent a tissue site to be treated. Attached to the distal end of the shaft is an electrode core capable of delivering a form of energy to the tissue site. The electrode includes one or more wires which extend from the proximal end of the shaft to the electrode core so that an energy source external to the patient can be coupled to the wire for delivering energy to the electrode core. A head which consists of a porous material at least partially surrounds the electrode core. In one variation, the head completely surrounds the electrode core. Extending through the shaft to the head is a lumen for delivering energy conducting liquid to the head. In one variation of this embodiment, the electrode head also includes a soluble material which enhances the conductivity of the energy conducting liquid. For example, the head can include salt which is dissolved by water. In another variation, the electrode is deemed to include energy conducting liquid which has been passed through the lumen to the head and into the tissue site adjacent the head.

In another embodiment, a trocar is provided which may be used to deliver the electrode to the tissue site. The trocar includes a hollow member having a sharpened distal end capable of being introduced into a patient and a longitudinal channel extending to the hollow member distal end within which the electrode may be positioned. The trocar also includes a slot extending along the length of the longitudinal channel through which the shaft of the electrode can pass.

In another embodiment, a kit is provided which includes the above described electrode for treating tissue and the above trocar for delivering the electrode. An assembly comprising the electrode positioned within the trocar is also provided.

The present invention also relates to a method for delivering the electrode to a tissue site using the trocar and for treating the tissue site with the electrode at multiple times separated temporally by minutes, hours, days, weeks, months or years.

In one embodiment, the method is for positioning the electrode at a tissue site and includes the steps of positioning the electrode adjacent the distal end of the trocar, introducing the trocar into a patient such that the electrode is positioned at a desired tissue site, and removing the trocar from the tissue site while passing the shaft of the electrode through the slot in the trocar.

In another embodiment, the method is for applying energy to the tissue site using the electrode by delivering energy conducting liquid to the head of the electrode through the shaft, delivering energy conducting liquid from the head to tissue surrounding the head, and applying energy from an external energy source to the electrode core such that the energy is conducted from the electrode core through the energy conducting liquid to the tissue site.

In a variation of this embodiment, energy is applied to the tissue sites by the electrode at multiple different times by delivering energy conducting liquid to the head of the electrode through the shaft, delivering energy conducting liquid from the head to tissue surrounding the head, applying energy from an external energy source to the electrode core such that the energy is conducted from the electrode core through the energy conducting liquid to the tissue site, waiting a period of time, and then repeating the steps of delivering energy conducting liquid to the head of the electrode through the shaft, delivering energy conducting liquid from the head to tissue surrounding the head, applying energy from an external energy source to the electrode core such that the energy is conducted from the electrode core through the energy conducting liquid to the tissue site.

An embodiment of the apparatus of the present invention will now be described with regard to FIGS. 1–3.

Figure 1A:
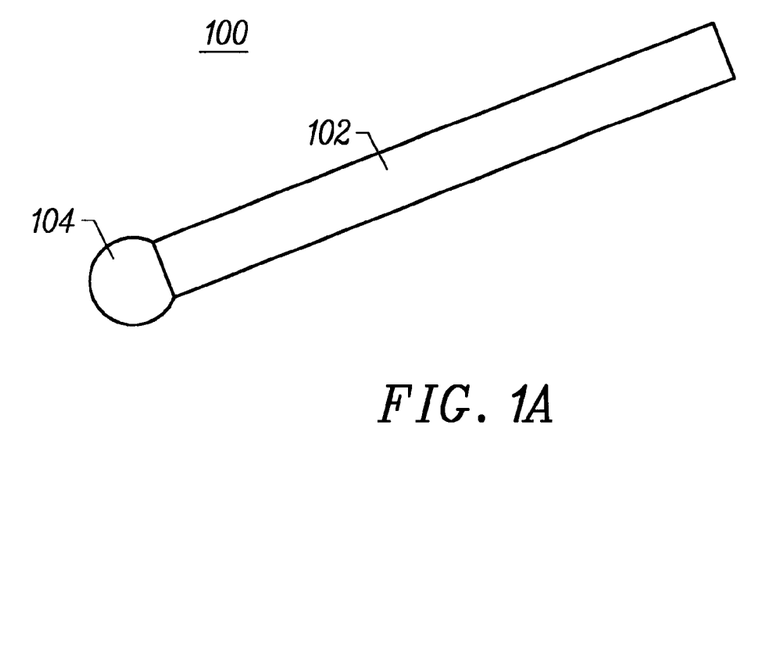
FIG. 1A is a side view of an electrode of the present invention.
Figure 1B:
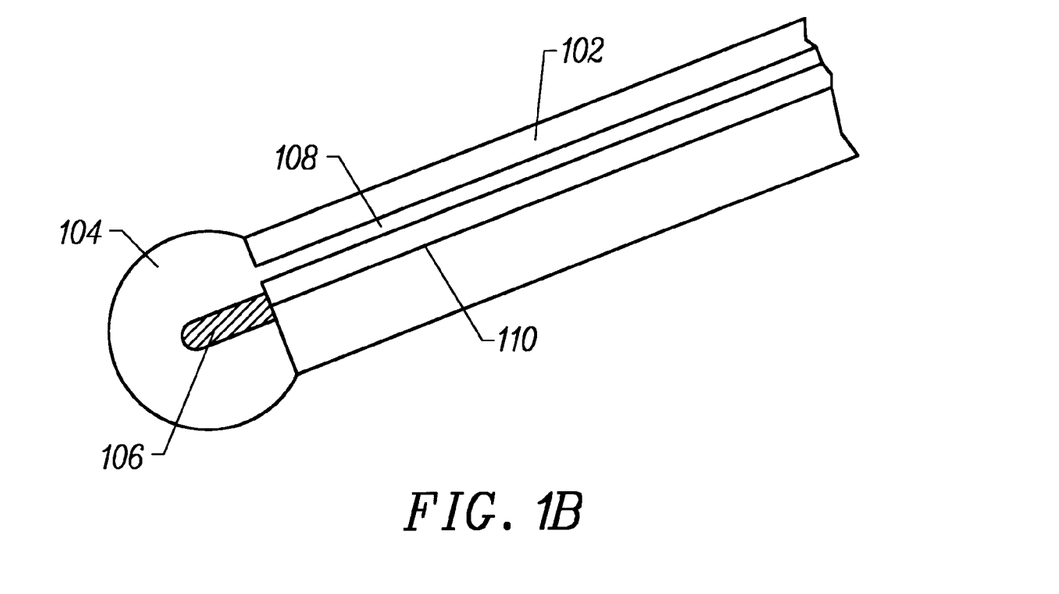
FIG. 1B is a cross-sectional view of the electrode of the present invention.

FIG. 1A provides a side view of an electrode 100 of the present invention which can be used to damage tissue and which can be left within the body of a patient between treatments. FIG. 1B provides a cross-sectional view of electrode 100. As illustrated, electrode 100 includes a shaft 102, a head 104 adjacent a distal end of the shaft 102, and an electrode core 106 coupled to the distal end of shaft 102 which is at least partially covered by the head 104.

Shaft 102 may be constructed of a sufficiently rigid, non-conducting, and biocompatible material, such as a polyolefin, tetrafluoroethylene, polyetheretherketone, or the like.

Head 104 may be formed of a porous material, such as a microporous membrane. Head 104 may also include a soluble material, such as sodium chloride (salt), which is solubilized when suitable liquid is passed through the head, such as water. The porous head material should be compatible with body tissue, as should the solubilizable head material.

Electrode core 106 is preferably constructed from a highly conductive and inert material such as platinum or titanium. The head 104 preferably at least partially surrounds the electrode core 106 coupled to the distal end of shaft 102. In a preferred embodiment, the head 104 completely surrounds the electrode core 106.

Electrode core 106 and head 104 may have any one of a variety of shapes and sizes, depending on the particular application and the shape and size of the targeted tissue area. In this regard, the electrode core and head may be shaped to match the targeted tissue site.

Electrode 100 also includes at least one lumen 108 which runs the length of shaft 102. Lumen 108 is in communication with the proximal end of shaft 102 and head 104. The number and positioning of lumens with respect to head 104 can be designed to produce a desired treatment zone or area. Electrode 100 also includes at least one wire 110 which runs the length of shaft 102. Wire 110 is coupled to electrode core 106 so as to allow a suitable energy source to be coupled to the proximal end of electrode 100 and provide energy through the wire 110 to electrode core 106.

The electrode can be operated as either a monopolar or bipolar electrode. When operated as a monopole, a single wire can be used. When operated as a dipole, multiple wires are needed.

Figure 2A:
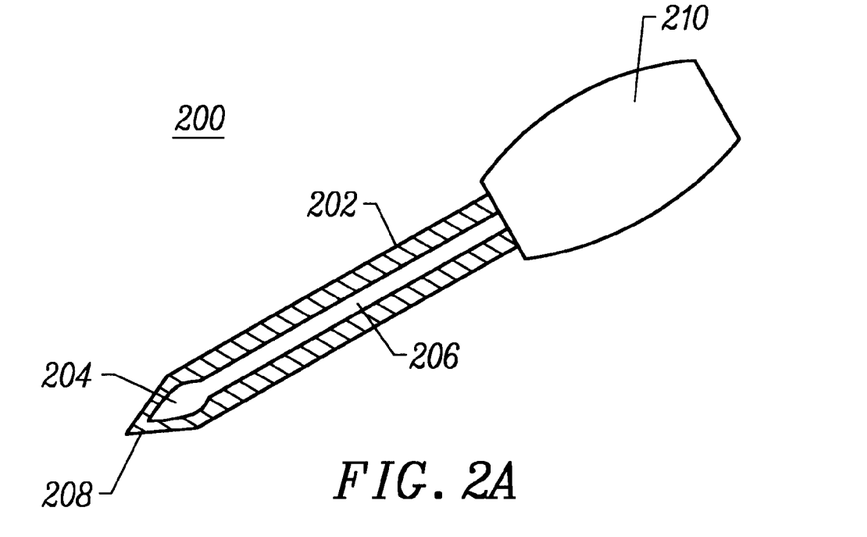
FIG. 2A is a side view of a trocar used with the present invention.
Figure 2B:
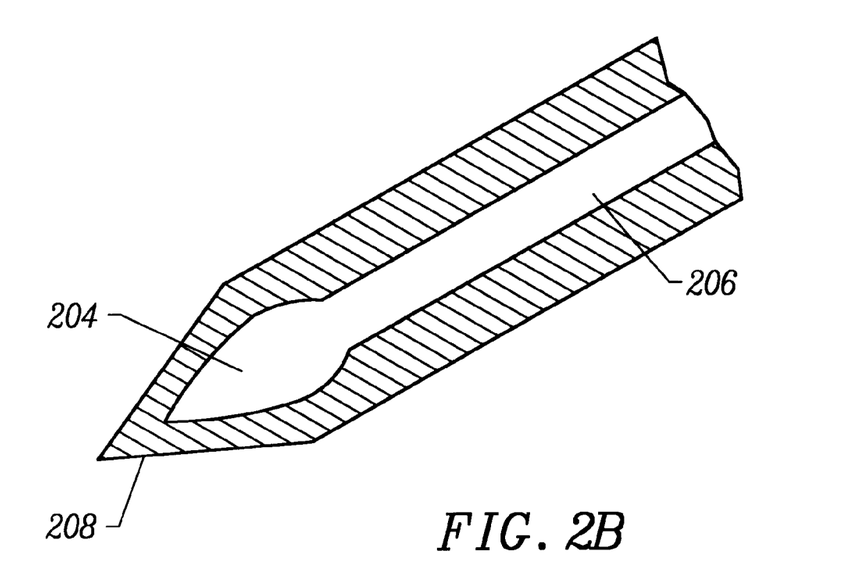
FIG. 2B is an expanded view of the distal end of the trocar used with the present invention.

FIG. 2A is a side view of a trocar 200 which may be used with the electrode of the present invention. FIG. 2B is an expanded view of the distal end of trocar 200. As illustrated, trocar 200 includes a hollow member 202 which has a longitudinal channel 204 and a slot 206 which runs the length of hollow member 202. Hollow member 202 has a distal end which has a sharpened point 208, and a proximal end which is coupled to a handle 210. The sharpened point 208 should enable the trocar to be introduced into a patient.

Figure 3:
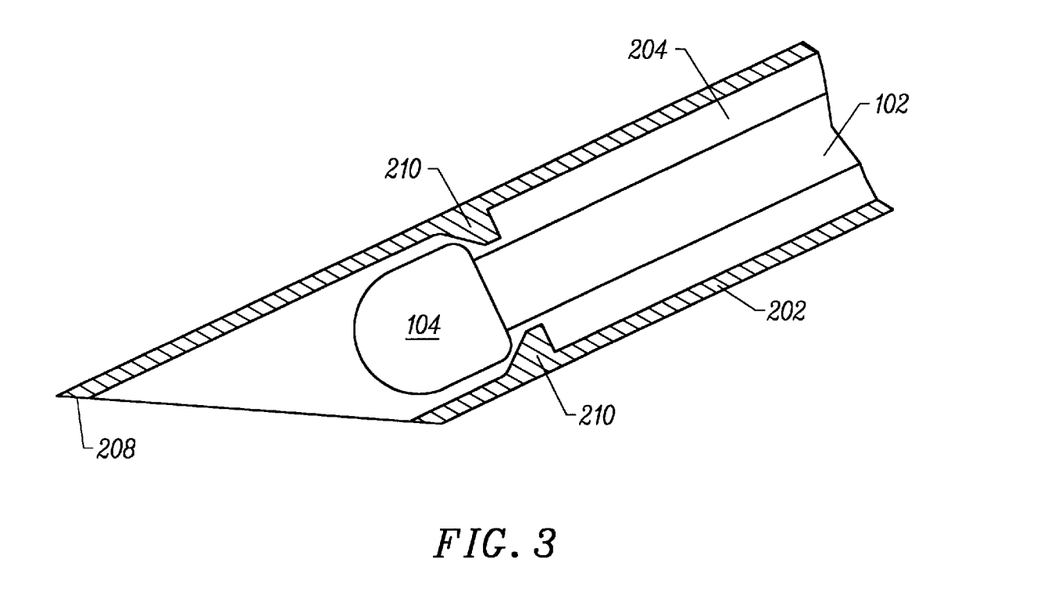
FIG. 3 is a cross-sectional view of the distal end of the trocar with the electrode in place.

FIG. 3 provides a cross-sectional view of the distal end of trocar 200 with the electrode 100 positioned in the trocar for delivering the electrode into a patient. Electrode 100 is introduced into the patient by using trocar 200 in this configuration. The physician places electrode 100 into hollow member 202 so shaft 102 runs along a channel 204 inside of hollow member 202.

As illustrated in FIG. 3, head 104 may have a larger diameter than shaft 102. In such instances, the inside diameter of hollow member 202 can be configured to be large enough to accommodate head 104. As also illustrated in FIG. 3, trocar can include a lip 210 within the interior of the distal end to prevent electrode 100 from sliding proximally within the trocar, thereby holding electrode 100 so head 104 remains at the distal end of hollow member 202 upon insertion of trocar 200 into the patient. If head 104 has a similar or smaller diameter than shaft 102, then channel 204 may have an appropriate length such that the proximal end of shaft 102 fits against the proximal end of channel 204 and prevents electrode 100 from sliding proximally within the trocar.

Figure 4A:
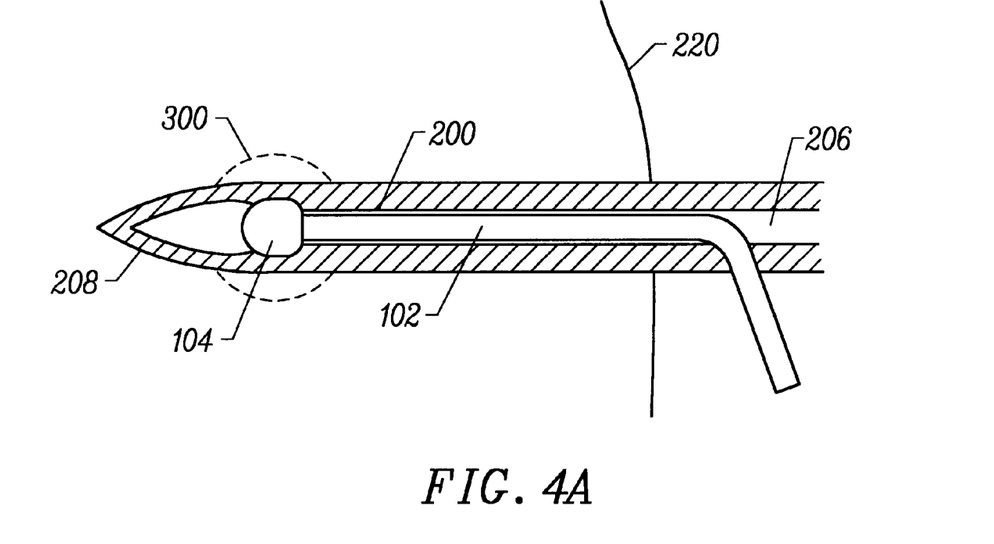
FIG. 4A illustrates a trocar with an implantable electrode delivered through the skin of a patient to a selected tissue site.

FIGS. 4A–4C illustrate electrode 100 being implanted into a patient using trocar 200. As illustrated in FIG. 4A, a physician introduces trocar through skin 220 of a patient and uses the sharpened point 208 of the trocar to place head 104 of electrode 100 at a selected tissue site 300. Selected site 300 may be a cancerous tumor, an abscess, infected tissue, or other tissue which the physician desires to damage or destroy. The distal end of the trocar should be sufficiently sharp and have sufficient column strength to puncture and penetrate most tissue obstacles encountered during placement of electrode 100. A physician can use generally accepted techniques such as fluoroscopy, ultrasound, or manual palpitation to help place head 104 of the electrode 100 at selected site 300.

Figure 4B:
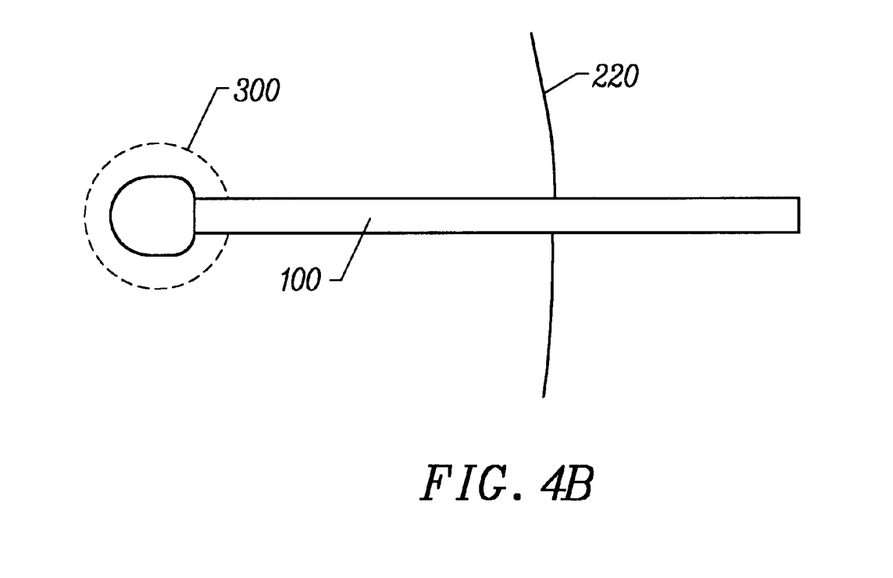
FIG. 4B illustrates an implantable electrode delivered through the skin of a patient to a selected tissue site with the trocar removed.

Once the physician locates head 104 at the selected tissue site 300, the trocar may be removed, leaving the electrode at the tissue site, as illustrated in FIG. 4B. Removal of the trocar may be performed by pulling the proximal end of shaft 102 through slot 206 in the trocar 200. Shaft 102 is preferably sufficiently flexible at its proximal end to allow the proximal end of the shaft 102 to be pulled through slot 206 of trocar 200. Shaft 102 may be tapered or thinner at its proximal end, or slot 206 may be wider at its proximal end, to facilitate pulling the proximal end of shaft 102 through slot 206 of trocar 200. Once the proximal end of shaft 102 is removed through slot 206 in the trocar 200, the proximal end of the shaft 102 is held in place as trocar 200 is removed from the patient's body by pulling outward on trocar 200. This motion causes shaft 102 to slide through slot 206 as trocar 200 is being pulled. The result is to remove trocar 200 from the patient's body so it can be set aside while leaving electrode 100 correctly positioned within the patient, as illustrated in FIG. 4B.

In order to help keep electrode 100 stationary as trocar 200 is withdrawn, shaft 102 may be manufactured to have sufficient column strength so that electrode 100 remains in place as trocar 200 is withdrawn from the patient. Multilumen polymers such as a polyolefin, tetrafluoroethylene, polyetheretherketone, and the like generally have the necessary column strength. In addition, these materials are known to be compatible with body tissues and are flexible enough that the patient will be comfortable while electrode 100 is within the patient.

Once trocar 200 has been removed, electrode 100 is in place for applying energy to treat and damage tissue adjacent electrode head 104. By forming electrode 100 of biocompatible materials, electrode 100 may be left within the patient for multiple treatments, each treatment being separated by minutes, hours, days, weeks, months or even years. If the physician needs to administer additional treatments to the patient, the physician does not need to perform the procedure of placing electrode 100 again. Thus, the invention reduces any difficulties which result from attempting to pierce the patient's skin multiple times and place electrode 100 multiple times within selected site 300.

Figure 5A:
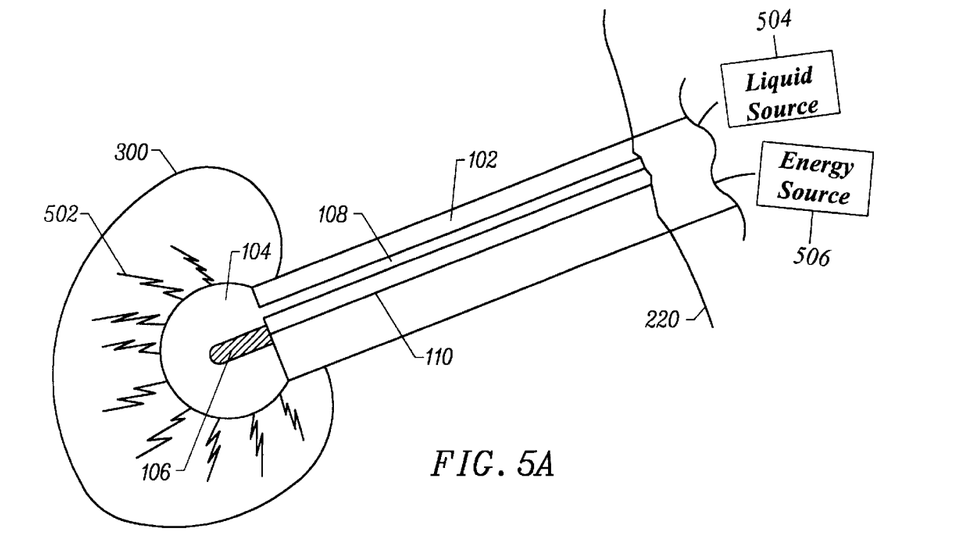
FIG. 5A illustrates the delivery of liquid through an implanted electrode to a selected tissue site.
Figure 5B:
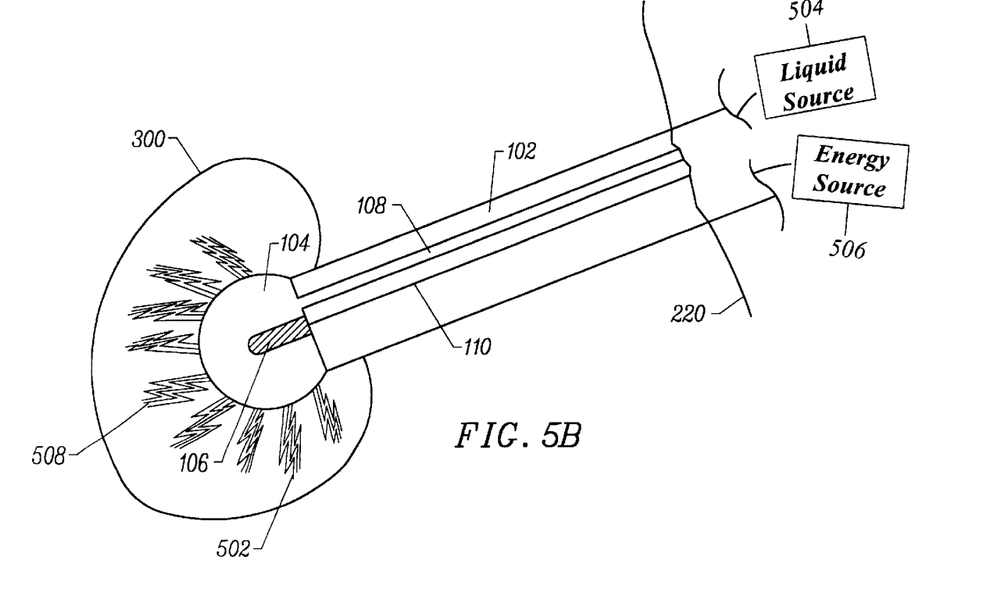
FIG. 5B illustrates the delivery of energy via the implanted electrode illustrated in FIG. 5A to the selected tissue site.

FIGS. 5A–5B illustrate using electrode 100 to treat and damage tissue by the application of energy. As illustrated in FIG. 5A, liquid 502 capable of conducting the form of energy being used is pumped through lumen 108 from liquid source 504. The liquid may be distilled water, saline solution, or the like. The liquid may be pumped by use of a syringe, a minipump, or the like. Pressure applied to the liquid 502 within lumen 108 will push the liquid through the porous material forming head 104. The liquid may begin to dissolve the soluble material in the head to further enhance the conductivity of the liquid. Thus, a conductive solution will flow from the head material and disperse through the tissue site 300 surrounding head 104. As illustrated in FIG. 5B, a suitable energy source 506, such as a radiofrequency energy source, is connected to wire 110 and electrode core 106, which in turn administers an energy 508 to selected site 300.

The use of a conductive solution is important to the operation of the present invention. Since the solution is conductive, the tissue which absorbs the solution will have a substantially enhanced electrical conductivity. The result is that tissue remote from surface of electrode 100 can be more easily treated at selected site 300 than if the solution were not used. Thus, the solution effectively increases the treatment area.

This increased treatment area occurs for several reasons. When a solution is not used, tissue adjacent to electrode 100 begins to desiccate very quickly. This desiccation occurs when tissue is exposed to a high current density. Without the conductive solution, a high current density is more likely to form because the current does not readily dissipate through the tissue and is spread mostly over the surface of electrode 100. When a conductive solution is used, the solution itself effectively becomes the surface of the electrode. Thus, the tissue which has absorbed the solution will be treated. Further, effectively increasing the size of electrode 100 reduces the current density which means desiccation is less likely to occur at the surface of electrode 10, providing additional treatment time. Additionally, using water in the conductive solution can rehydrate the tissue, which increases desiccation times even further. The additional time is desirable because it allows tissue to become heated from thermal conductivity as well as from the direct heating which results from RF energy flowing through the tissue.

Once the physician has completed the first treatment, the physician may leave electrode 100 in place within the patient by placing a sealing bandage over the wound where shaft 102 enters the patient. At a later time, the physician may perform additional diagnostic procedures such as X-rays, fluoroscopy, or ultrasound to determine if the target tissue was destroyed. If the target tissue was not completely destroyed, the physician may perform subsequent treatments by removing the sealing bandage to access shaft 102 of electrode 100. If the physician finds the target tissue was completely destroyed, the physician can remove the sealing bandage, grasp shaft 102, and pull electrode 100 directly from the patient.

To minimize patient discomfort while the physician removes electrode 100 from the patient, shaft 102 can be coated with a compound that resists the tendency of tissues to attach to shaft 102. If tissue does not attach to shaft 102, electrode 100 will slide from the patient with less resistance, which will make it easier for a physician to remove electrode 100. These types of slippery agents are available and may consist of a combination of silicone, heparin, or the like. Shaft 102 may also be coated with an antibiotic to prevent infection at the point where shaft 102 enters the skin of the patient.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An implantable electrode for treating tissue in a patient with energy comprising:

a shaft having a length sufficient to extend from outside a body of the patient to adjacent a tissue site to be treated;

an electrode core attached to a distal end of the shaft capable of delivering a form of energy to the tissue site to damage the tissue;

one or more wires which extend from a proximal end of the shaft to the electrode core such that an energy source external to the patient can be coupled to the wire for delivering energy to the electrode core; and a head formed at least in part of a porous material which at least partially surrounds the electrode core;

the shaft including a lumen for delivering energy conducting liquid from outside the body through the head to the tissue site the electrode head being formed of a soluble material which is solubilized when the energy conducting liquid is delivered and enhances the conductivity of the energy conducting liquid.

2. The electrode according to claim 1 wherein the electrode head surrounds the electrode core.

3. A kit for delivering an implantable electrode to a tissue site comprising:

an implantable electrode which includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a soluble material which at least partially surrounds the electrode core, wherein the shaft also includes a lumen for delivering energy conducting liquid from outside the body to the head; and a trocar for delivering the implantable electrode to a tissue site which includes a hollow member having a sharpened distal end capable of being introduced into a patient and a longitudinal channel extending to a hollow member distal end within which an implantable electrode may be positioned, and a slot extending along a length of the longitudinal channel through which the shaft of the electrode can pass and the trocar can be removed without removing the implantable electrode.

4. The kit according to claim 3 wherein the electrode head is also formed of a soluble material which is solubilized when the energy conducting liquid is delivered and enhances the conductivity of the energy conducting liquid.

5. The kit according to claim 3 wherein the electrode head surrounds the electrode core.

6. An assembly for delivering an implantable electrode to a tissue site comprising:

a trocar which includes a hollow member having a sharpened distal end capable of being introduced into a patient and a longitudinal channel extending to a hollow member distal end within which an implantable electrode may be positioned, and a slot extending along a length of the longitudinal channel through which a shaft of the implantable electrode can pass and the trocar can be removed without removing the implantable electrode; and an implantable electrode positioned within the trocar hollow member which includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a soluble material which at least partially surrounds the electrode core, wherein the shaft also includes a lumen for delivering energy conducting liquid from outside the body to the head.

7. The assembly according to claim 6 wherein the electrode head is also formed of a soluble material which is solubilized when the energy conducting liquid is delivered and enhances the conductivity of the energy conducting liquid.

8. The assembly according to claim 6 wherein the electrode head surrounds the electrode core.

9. A method for introducing an implantable electrode at a selected tissue site comprising:

providing an implantable electrode which includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a porous material which at least partially surrounds the electrode core, wherein the shaft includes a lumen for delivering energy conducting liquid from outside the body to the head;

placing the implantable electrode in a trocar having a sharpened distal end capable of being introduced into a patient, a hollow member having a longitudinal channel within which an implantable electrode may be positioned, and a slot extending from the distal end of the trocar along a length of the longitudinal channel through which the shaft of the implantable electrode can pass;

inserting the trocar into a patient such that the head of the implantable electrode is positioned at the selected tissue site; and removing the trocar while passing the shaft through the longitudinal channel such that the head of the implantable electrode remains positioned at the selected tissue site and a proximal end of the shaft extends outside the body.

10. The method according to claim 9 wherein the electrode head is also formed of a soluble material which is solubilized when the energy conducting liquid is delivered and enhances the conductivity of the energy conducting liquid.

11. The method according to claim 9 wherein the electrode head surrounds the electrode core.

12. A method for damaging tissue at a selected tissue site comprising:

providing an implantable electrode at a selected tissue site which includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a porous material which at least partially surrounds the electrode core, wherein the shaft includes a lumen for delivering energy conducting liquid from outside the body to the head, the electrode head also being formed of a soluble material which is solubilized when the energy conducting liquid is delivered and enhances the conductivity of the energy conducting liquid;

delivering energy conducting liquid through the lumen to create a region containing a conductive solution in the vicinity of the head; and delivering energy from an external energy source to the electrode which delivers energy to the selected tissue site.

13. The method according to claim 12 wherein the electrode head surrounds the electrode core.

14. A method for damaging tissue at a selected tissue site at different times using an implantable electrode comprising:

providing an implantable electrode at a selected tissue site which includes a shaft having a length sufficient to extend from outside a body of the patient to adjacent a tissue site to be treated, an electrode core attached to a distal end of the shaft capable of delivering a form of energy to the tissue site, one or more wires which extend from a proximal end of the shaft to the electrode core such that an energy source external to the patient can be coupled to the wire for delivering energy to the electrode core, and a head formed at least in part of a porous material which at least partially surrounds the electrode core, wherein the shaft includes a lumen for delivering energy conducting liquid from outside the body to the head;

delivering energy conducting liquid through the lumen to create a region containing a conductive solution in the vicinity of the head;

delivering energy from an external energy source to the electrode which delivers energy to the selected tissue site, waiting a period of time;

delivering energy conducting liquid through the lumen to at least partially dissolve the head and create a region containing a conductive solution in the vicinity of the head; and delivering energy from an external energy source to the electrode which delivers energy to the selected tissue site.

15. The method according to claim 14 wherein the electrode head is also formed of a soluble material which is solubilized when the energy conducting liquid is delivered and enhances the conductivity of the energy conducting liquid.

16. The method according to claim 14 wherein the electrode head surrounds the electrode core.

17. The method according to claim 14 wherein the period of time is selected from the group consisting of minutes, hours, days, weeks, months and years.

* * * * *